United States Patent [19]  
Nakazawa et al.

[11] Patent Number: 4,564,676  
[45] Date of Patent: Jan. 14, 1986

[54] PROCESS FOR PREPARING CEPHALOSPORIN DERIVATIVES

[75] Inventors: Junichi Nakazawa; Teruo Hashimoto; Masanao Kaneko; Takeo Miyaoka, all of Hiromachi, Japan

[73] Assignee: Sankyo Company Limited, Tokyo, Japan

[21] Appl. No.: 477,836

[22] Filed: Mar. 23, 1983

Related U.S. Application Data

[63] Continuation of Ser. No. 233,678, Feb. 11, 1981, abandoned, which is a continuation of Ser. No. 70,804, Aug. 29, 1979, abandoned.

[30] Foreign Application Priority Data

Sep. 22, 1978 [JP] Japan ............................. 53-116898

[51] Int. Cl.$^4$ ............................................ C07D 501/04
[52] U.S. Cl. .................................. 544/21; 544/16/22; 544/26/27
[58] Field of Search ................ 424/246; 544/21, 26, 544/27, 16, 22

[56] References Cited

U.S. PATENT DOCUMENTS 3,840,531 10/1974 Green .................................. 544/26
4,014,874 3/1977 Peter et al. ........................ 544/27
4,144,391 3/1979 Hatfield et al. .................... 544/16
4,165,429 8/1979 Iwanami et al. .................... 544/21
4,312,986 1/1982 Saikawa et al. .................... 544/27
4,317,907 3/1982 Saikawa et al. .................... 544/27

Primary Examiner—Nicholas S. Rizzo  
Attorney, Agent, or Firm—Frishauf, Holtz, Goodman & Woodward

[57] ABSTRACT

A 7-acylamino (or 7-amino)-3-(substituted thiomethyl)-cephalosporin derivative or a carboxyl derivative thereof is prepared by heating the corresponding 7-acylamino (or 7-amino)-3-carbamoyloxymethylcephalosporanic acid or a carboxyl derivative thereof with a thiol corresponding to the group which it is desired to introduce at the 3-position under conditions in which the water present is minimized, specifically, either no water is present or the amount of water is limited to less than 5 times the weight of the 7-acylamino (or 7-amino)-3-carbamoyloxymethylcephalosporanic acid or carboxyl derivative thereof. The compounds thus prepared are useful as pharmaceuticals or as intermediates in the production of pharmaceuticals. One of the compounds thus prepared, namely 7α-methoxy-3-(1-methyl-1H-tetrazol-5-yl)thiomethyl-7β-(O-5-p-nitrobenzoylamino-5-carboxyvaleramido-3-cephem-4-carboxylic acid, is a new compound and it and its salts and esters also form part of the present invention.

13 Claims, No Drawings

PROCESS FOR PREPARING CEPHALOSPORIN DERIVATIVES

This application is a continuation of application Ser. No. 233,678, filed Feb. 11, 1981 (now abandoned) which was a continuation of application Ser. No. 70,804, filed Aug. 29, 1979 (now abandoned).

BACKGROUND TO THE INVENTION

The present invention relates to a new process for preparing a series of cephalosporin derivatives by replacing a carbamoyloxymethyl group at the 3-position of a 7-acylaminocephalosporin derivative by a substituted thiomethyl group.

Numerous 7-acylaminocephalosporin compounds have been prepared and many are known to have bacterial activity. In particular, certain cephalosporins having a heterocyclic thiomethyl group (for example a thiazolylthiomethyl group or a tetrazolylthiomethyl group) have been found to possess particularly effective antibacterial activity.

Accordingly, many processes have been proposed for replacing substituents at the 3-position of various cephalosporin compounds by heterocyclic thiomethyl groups. Among the techniques which have been proposed are the following:

1. Reacting a cephalosporin compound having an acetoxymethyl group at its 3-position with a heterocyclic thiol, as disclosed in "Cephalosporins and Penicillins—Chemistry and Biology", edited by Edwin H. Flynn, pages 158–159, Japanese Patent Publications Nos. 39-17936 and 49-45880, and Japanese Patent Application (laid open) No. 50-154287.

2. Reacting a cephalosporin compound having a carbamoyloxymethyl group at its 3-position with a heterocyclic thiol, as disclosed in Japanese Patent Application (laid open) No. 50-83383.

In the two methods described above, the reactions are carried out in water or in an aqueous organic solvent at a pH of 6–7, the amount of water used in these proposals generally being from 10 to 30 times the weight of the starting material.

More recently, cephalosporin compounds having a methoxy group at the 7α-position have been developed and certain of these have been reported to have potent antibacterial activity against a wide range of bacteria. Many of these compounds have a substituted thiomethyl group at the 3-position of the cephem nucleus and most are initially prepared from cephamycin C. As cephamycin C has a carbamoyloxymethyl group at its 3-position, this group has to be replaced by a substituted thiomethyl group. Known methods of effecting this replacement, such as those described above, give low yields and are commercially unattractive.

There has recently been published in Japanese Patent Application (laid-open) No. 53-98987 a proposal to replace the carbamoyloxymethyl group at the 3-position of cephalosporin compounds by a substituted thiomethyl group by reacting the cephalosporin compound with a suitable thiol in the presence of boron trifluoride or a complex thereof in an organic solvent without using water or an aqueous organic solvent. However, 7α-methoxycephalosporin compounds are decomposed by boron trifluoride and this method cannot, therefore, be used with such compounds.

There is, therefore, a need for a process which is capable of replacing a carbamoyloxymethyl group at the 3-position of a cephalosporin compound (whether or not it has a 7-methoxy group) without decomposing the compound and giving the desired product in high yield.

BRIEF SUMMARY OF INVENTION

We have surprisingly found that the replacement of the carbamoyloxymethyl group at the 3-position of cephalosporin compounds by a substituted thiomethyl group can be carried out by reacting the cephalosporin compound with a thiol non-catalytically either in the complete absence of water or, where water is present, in an amount of water not exceeding 5 times the weight of the cephalosporin compound.

Thus, the present invention provides a non-catalytic process for the preparation of a cephalosporin derivative of formula (I):

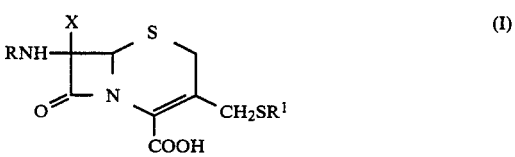

(in which:

R represents a hydrogen atom or an acyl group;

$R^1$ represents a substituted or unsubstituted heterocyclic group or the group

and

X represents a hydrogen atom or an alkoxy group) or a carboxyl derivative thereof which process comprises heating a cephalosporin compound of formula (II):

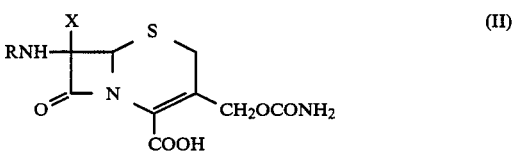

(in which R and X are as defined above) or a carboxyl derivative thereof with a thiol of formula (III):

 $R^1SH$     (III)

(in which $R^1$ is as defined above) under such conditions that water, if present, does not exceed 5 times the weight of said compound (II).

The process of the invention, in which the reaction is carried out under conditions of minimal water content, enables substantially increased yields and much reduced reaction times to be achieved, when compared with the prior art processes. For example, if cephamycin C (which is a cephalosporin derivative having a 7α-methoxy group) or a cephamycin C derivative having a protected 7β-amino group is reacted with a thiol under prior art conditions, in the presence of water in an amount of from 10 to 30 times the weight of the starting cephamycin C or derivative thereof at a temperature of 50°–60° C., the desired product is obtained in a yield of only 25–30% of theory and the reaction requires from 4 to 6 hours; moreover both the starting material and the desired product are observed to decompose. On the other hand, if the same reaction is carried out using water in an amount less than 5 times the weight of the cephamycin C starting material or in the complete absence of water, yields increase sharply and the product can be obtained in yields of 80% or even more. The time required for the reaction is also greatly decreased and the reaction will normally be complete within from 5 to 15 minutes.

DETAILED DESCRIPTION OF INVENTION

The preferred compounds of formula (II) used as starting materials in the process of the invention are 7β-amino-7α-alkoxy-3-carbamoyloxymethyl-3-cephem-4-carboxylic acids, 7β-amino-3-carbamoyloxymethyl-3-cephem-4-carboxylic acids, 7β-acylamino-7α-alkoxy-3-carbamoyloxymethyl-3-cephem-4-carboxylic acids and 7β-acylamino-3-carbamoyloxymethyl-3-cephem-4-carboxylic acids as well as carboxyl derivatives thereof. Since the acyl group on the amino group at the 7β-position of these compounds does not participate in the reaction, any type of acyl group may be present and a wide range of such groups is well-known to those skilled in the art. For example, it may be a substituted acetyl group, a substituted valeryl group or a substituted benzoyl group or any of these groups which are unsubstituted. Where it is a substituted acetyl group, the substituents may be one or more of the following: amino groups, substituted amino groups, carboxyl groups, halogen atoms, sulphonyl groups, hydroxyl groups, heterocyclic groups, heterocyclic-thio groups, heterocyclic-oxy groups, substituted or unsubstituted alkylthio groups or alkynylthio groups. Where the acyl group is a substituted valeryl group, the substituents may be one or more of the following: nitro groups, amino groups or carboxyl groups. Where the acyl group is a substituted benzoyl group, the substituents may be one or more of the following: amino groups, hydroxyl groups and sulpho groups.

The process of the invention is particularly useful for replacing the carbamoyloxymethyl group at the 3-position of 7α-alkoxycephalosporin compounds by substituted thiomethyl groups and, accordingly, the preferred starting materials are 7β-acylamino-7α-alkoxy-3-carbamoyloxymethyl-3-cephem-4-carboxylic acids, that is to say compounds of formula (IV):

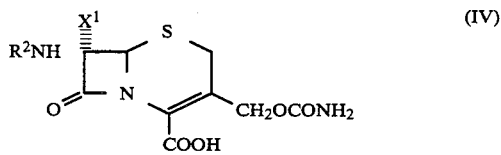

(in which $R^2$ represents an acyl group and $X^1$ represents an alkoxy group), as well as carboxyl derivatives thereof.

Specific examples of compounds of formula (II) which may be used as starting materials in the process of the invention are:
cephamycin C;
7β-(D-5-p-nitrobenzoylamino-5-carboxyvaleramido)-7α-methoxy-3-carbamoyloxymethyl-3-cephem-4-carboxylic acid;
7β-(D-5-isobutoxycarbonylamino-5-carboxyvaleramido)-7α-methoxy-3-carbamoyloxymethyl-3-cephem-4-carboxylic acid;
7β-(imidazol-2-yl)thioacetamido-7α-methoxy-3-carbamoyloxymethyl-3-cephem-4-carboxylic acid;
7β-(1,3,4-thiadiazol-2-yl)thioacetamido-7α-methoxy-3-carbamoyloxymethyl-3-cephem-4-carboxylic acid;
7β-(isoxazol-3-yloxy)acetamido-7α-methoxy-3-carbamoyloxymethyl-3-cephem-4-carboxylic acid;
7β-propargylthioacetamido-7α-methoxy-3-carbamoyloxymethyl-3-cephem-4-carboxylic acid;
7β-cyanomethylthioacetamido-7α-methoxy-3-carbamoyloxymethyl-3-cephem-4-carboxylic acid;
7β-(5-methyl-1,3,4-thiadiazol-2-yl)thioacetamido-7α-methoxy-3-carbamoyloxymethyl-3-cephem-4-carboxylic acid; and
7β-(4H-1,2,4-triazol-3-yl)thioacetamido-7α-methoxy-3-carbamoyloxymethyl-3-cephem-4-carboxylic acid, as well as carboxyl derivatives thereof.

The term "carboxyl derivative" means a compound in which the hydroxyl group of the carboxyl group at the 4-position of the cephem nucleus is replaced by another group. Since the carboxyl group does not take part in the reaction, a wide variety of carboxyl derivatives may be employed and such derivatives are well-known to those skilled in the art. Examples include:

(a) any ester which does not affect the reaction, for example substituted or unsubstituted alkyl esters (such as methyl, ethyl, propyl, isopropyl, butyl, t-butyl, methoxymethyl, ethoxymethyl, phenoxymethyl, methylthiomethyl, phenylthiomethyl, dimethylaminoethyl, diethylaminoethyl, phenacyl, p-bromophenacyl, acetoxymethyl, pivaloyloxymethyl, benzoyloxymethyl, 1,1-diacetylalkyl, methanesulphonylethyl, toluenesulphonylethyl, trichloroethyl, cyanoethyl or phthalimidomethyl esters), cycloalkyl esters, cycloalkenyl esters and trimethylsilyl esters;

(b) any amide which does not affect the reaction;

(c) except where the reaction is carried out in the presence of water, any acid anhydride, for example a mixed acid anhydride with an organic or inorganic acid or an anhydride formed by reacting the carboxyl group with a compound such as hydroxysuccinimide, N-hydroxyphthalimide or a dialkylhydroxylamine.

The thiols of formula (III) which are the other reagents used in the process of the invention are thioureas or substituted or unsubstituted heterocyclic thiols. In the case of heterocyclic thiols, the heterocyclic group may be any such group which commonly forms part of a heterocyclic thiomethyl group in known cephalosporin derivatives. Preferred heterocyclic groups contain 5 or 6 ring atoms including: from 1 to 4 nitrogen atoms; 1 oxygen atom and 1 or 2 nitrogen atoms; or 1 sulphur atom and 1 or 2 nitrogen atoms. These heterocyclic groups may be unsubstituted or may have from 1 to 3 alkyl substituents. Representative examples of thiols containing such heterocyclic groups are 1-methyl-5-mercaptotetrazole, 5-methyl-2-mercapto-1,3,4-thiadiazole and 3-mercapto-1,2,4-triazole.

The reaction between the thiol (III) and the cephalosporin compound (II) or carboxyl derivative thereof will proceed simply upon mixing and heating the two reagents under anhydrous conditions or in the presence of a small amount of water. Where water is employed, the amount used is preferably the minimum required to allow mechanical stirring of the mixture and, in any case, is less than 5 times the weight of the compound of formula (II). A preferred amount of water is from 0.1 to 2 times the weight of the compound of formula (II).

The reaction temperature is preferably from 50° C. to 150° C., although the precise temperature chosen will depend upon the reagents and on the presence or absence of water. Thus, if water is present, a more preferred temperature range is from 65° to 90° C. On the other hand, if no water is present, a more preferred temperature range may be from 65° to 90° C. similarly to that in case where water is present.

The time required for the reaction will depend upon the nature of the reagents and the reaction temperature; the reaction will normally require from several seconds to several tens of minutes, although in most cases the reaction will be complete within 15 minutes. It is best to allow the reaction to continue for a period of from 5 to 15 minutes.

At the end of the period allowed for the reaction, the desired product may be recovered from the reaction mixture by conventional means. For example, where the reaction is carried out in the presence of water, the following sequence is preferably employed: water and a water-immiscible organic solvent (such as ethyl acetate) are added to the reaction mixture; the aqueous phase is then acidified and extracted with an organic solvent; the solvent is then distilled off from the extract under reduced pressure to give the desired product. Where the reaction is carried out in the absence of water, the desired product may be obtained from the reaction mixture substantially in the same manner as done in case where the reaction is effected in the presence of water. Whichever method is employed to recover the desired compound, it may be, and preferably is, subsequently further purified by conventional means such as chromatography.

Where a carboxyl derivative of the compound of formula (II) is employed, the product is a carboxyl derivative of the compound of formula (I). If desired, this derivative may be converted to the compound (I) itself by methods well-known in the art, e.g. deesterification or hydrolysis.

If desired, the compound obtained by the process of the invention can be converted to a salt thereof by conventional means; this salification may take place before or after isolation of the compound from the reaction mixture. Suitable salts include inorganic salts (e.g. lithium, sodium, potassium, calcium, magnesium or or ammonium salts) or organic amine salts (e.g. cyclohexylammonium, diisopropylammonium or triethylammonium salts), although sodium and potassium salts are preferred.

Of the compounds prepared by the process of the invention, the following are known to have antibacterial activity:

1. 7β-(imidazol-2-yl)thioacetamido-7α-methoxy-3-(1-methyl-1H-tetrazol-5-yl)thiomethyl-3-cephem-4-carboxylic acid;
2. 7α-methoxy-3-(1-methyl-1H-tetrazol-5-yl)thiomethyl-7β-(1,3,4-thiadiazol-2-yl)thioacetamido-3-cephem-4-carboxylic acid;
3. 7β-(isoxazol-5-yloxy)acetamido-7α-methoxy-3-(1-methyl-1H-tetrazol-5-yl)thiomethyl-3-cephem-4-carboxylic acid;
4. 7α-methoxy-3-(1-methyl-1H-tetrazol-5-yl)thiomethyl-7β-propargylthioacetamido-3-cephem-4-carboxylic acid;
5. 7β-cyanomethylthioacetamido-7α-methoxy-3-(1-methyl-1H-tetrazol-5-yl)thiomethyl-3-cephem-4-carboxylic acid;
6. 7α-methoxy-3-(1-methyl-1H-tetrazol-5-yl)thiomethyl-7β-(5-methyl-1,3,4-thiadiazol-2-yl)thioacetamido-3-cephem-4-carboxylic acid.

The following compounds, which can be prepared by the process of the invention, are useful as intermediates in the synthesis of other antibacterial agents:

7. 7β-(D-5-amino-5-carboxyvaleramido)-7α-methoxy-3-(1-methyl-1H-tetrazol-5-yl)thiomethyl-3-cephem-4-carboxylic acid;
8. 7β-(D-5-isobutoxycarbonylamino-5-carboxyvaleramido)-7α-methoxy-3-(1-methyl-1H-tetrazol-5-yl)thiomethyl-3-cephem-4-carboxylic acid;
9. 7α-methoxy-3-(1-methyl-1H-tetrazol-5-yl)thiomethyl-7β-(D-5-p-nitrobenzoylamino-5-carboxyvaleramido)-3-cephem-4-carboxylic acid.

Of the compounds listed above, Compound No. 9 is a per se new compound and it, and its salts and esters, also form part of the present invention.

The process of the invention is illustrated by the following non-limiting examples.

EXAMPLE 1

To 1.0 g (1.83 mmole) of 7β-(D-5-isobutoxycarbonylamino-5-carboxyvaleramido)-7α-methoxy-3-carbamoyloxymethyl-3-cephem-4-carboxylic acid (purity 83%) were added 0.5 g of 1-methyl-5-mercaptotetrazole and 20 ml of acetone, and then the solvent was distilled off under reduced pressure. The resulting oily residue was heated on an oil bath at a temperature of 120° C. for 5 minutes, after which cooled diisopropyl ether was added to the reaction mixture. The mixture was thoroughly stirred and filtered and the precipitate was washed with, in turn, diisopropyl ether and diethyl ether. The powder thus obtained was dissolved in 10 ml of acetone, and 2.5 ml of a 1 mmole/ml solution of sodium 2-ethylhexanoate in ethyl acetate were added to the resulting solution. The crystalline powder which precipitated was collected by filtration, washed with acetone and dried to give 1.1 g (yield 82%) of disodium 7β-(D-5-isobutoxycarbonylamino-5-carboxyvaleramido)-7α-methoxy-3-(1-methyl-1H-tetrazol-5-yl)thiomethyl-3-cephem-4-carboxylate of purity 73.1%.

Nuclear Magnetic Resonance Spectrum (D$_2$O) δ ppm: 0.92, 1.03 (doublet, 6H); 1.7–2.78 (multiplet, 7H); 3.66 (singlet, 3H); 4.18 (singlet, 3H); 5.3 (singlet, 1H).

EXAMPLE 2

To 1.0 g of 3-carbamoyloxymethyl-7α-methoxy-7β-(D-5-methoxycarbonylamino-5-carboxyvaleramido)-3-cephem-4-carboxylic acid (purity 80%) were added 0.5 g of 1-methyl-5-mercaptotetrazole and 20 ml of acetone. The mixture was then treated as described in Example 1 to give 1.16 g of 7β-(D-5-methoxycarbonylamino-5-carboxyvaleramido)-7α-methoxy-3-(1-methyl-1H-tetrazol-5-yl)thiomethyl-3-cephem-4-carboxylic acid. The purity of the product was 65%, determined by high speed liquid chromatography through a column containing Bondapack C-18 (a trade name for a silicone polymer column packing material available from Waters Co. Limited, U.S.A.) using as solvent a 18% v/v aqueous acetonitrile solution containing 2 ml/liter of pic A (a trade name for a grade of tetrabutylammonium phosphate suitable for paired-ion chromatography, available from Waters Co. Limited, U.S..). The product contained small amounts of 1-methyl-5-mercaptotetrazole and was obtained in a yield of 84.9%.

Nuclear Magntic Resonance Spectrum (CD$_3$OD) δ ppm: 1.53–2.66 (multiplet, 7H); 3.56 (singlet, 3H); 3.7 (singlet, 3H); 4.07 (singlet, 3H); 5.15 (singlet, 1H).

EXAMPLE 3

To 2.0 g of 3-carbamoyloxymethyl-7β-cyanomethyl-thioacetamido-7α-methoxy-3-cephem-4-carboxylic acid were added 1.5 g of 1-methyl-5-mercaptotetrazole and 20 ml of acetone, and then the mixture was evaporated to dryness under reduced pressure. The oily residue was heated to bubbling on a oil bath at a bath temperature of 120° C. for about 10 minutes, after which the reaction mixture was cooled and dissolved in a very small amount of acetone. To the solution were added 50 ml of diisopropyl ether and the mixture was thoroughly stirred to solidify the oily substance. The resulting solid was collected by filtration and dissolved in 20 ml of acetone. To the solution was added 1.0 g of dicyclohexylamine and then the solvent was distilled off under reduced pressure. Diisopropyl ether was added to the oily residue to solidify the oil. A small amount of ethanol was added to the solid and the mixture was allowed to stand to crystallize. The crystals were collected by filtration, washed with a small amount of ethanol and dried to give dicyclohexylammonium 7β-cyanomethyl-thioacetamido-7α-methoxy-3-(1-methyl-1H-tetrazol-5-yl)thiomethyl-3-cephem-4-carboxylate in a yield of 70.2%. Melting point 155° C.

Nuclear Magnetic Resonance Spectrum (CDCl$_3$: CD$_3$OD=1:1 by volume) δ ppm: 1.03–2.31 (multiplet, 22H); 3.53 (singlet, 2H); 3.58 (singlet, 3H); 3.7 (singlet, 2H); 4.0 (singlet, 3H); 5.09 (singlet, 1H).

EXAMPLE 4

1.0 g of 1-methyl-5-mercaptotetrazole was added to 1.0 g of 3-carbamoyloxymethyl-7α-methoxy-7β-thienylacetamido-3-cephem-4-carboxylic acid, and the mixture was well stirred and then heated on an oil bath at 120° C. for 5 minutes. After cooling the reaction mixture, it was dissolved in acetone and then the acetone was distilled off until the mixture became syrupy. Diisopropyl ether was added to the residue and then the mixture was thoroughly stirred to solidify the oily substance. This solid was collected by filtration, washed, in turn, with diisopropyl ether and with diethyl ether and then dried to give 0.97 g (yield 85.9%) of 7α-methoxy-3-(1-methyl-1H-tetrazol-5-yl)thiomethyl-7β-thienylacetamido-3-cephem-4-carboxylic acid.

Nuclear Magnetic Resonance Spectrum (CD$_3$OD) δ ppm: 3.48 (singlet, 3H); 3.98 (singlet, 2H); 4.0 (singlet, 3H); 4.22–4.73 (quartet, 2H, J=14 Hz); 5.11 (singlet, 1H); 6.91–7.5 (multiplet, 3H).

EXAMPLE 5

To 1.0 g of 3-carbamoyloxymethyl-7β-(D-5-isobutoxycarbonylamino-5-carboxyvaleramido)-7α-methoxy-3-cephem-4-carboxylic acid were added 1.0 g of 2-methyl-5-mercapto-1,3,4-thiadiazole and 3 ml of toluene, and then the mixture was heated on an oil bath at a bath temperature of 115°–120° C. for 10 minutes. After cooling the reaction mixture, it was thoroughly stirred to produce a powder, which was collected by filtration, washed with diethyl ether and dried to give 1.0 g of 7β-(D-5-isobutoxycarbonylamino-5-carboxyvaleramido)-7α-methoxy-3-(1-methyl-1,3,4-thiadiazol-5-yl)thiomethyl-3-cephem-4-carboxylic acid, a yield of 91%.

Nuclear Magnetic Resonance Spectrum (CD$_3$OD) δ ppm: 1.08, 1.18 (doublet, 6H); 1.6–2.6 (multiplet, 7H); 2.76 (singlet, 3H); 3.57 (singlet, 3H); 5.11 (singlet, 1H).

EXAMPLE 6

3.0 g of 1-methyl-5-mercaptotetrazole and 1 ml of water were added to 3.0 g of 3-carbamoyloxymethyl-7β-(D-5-isobutoxycarbonylamino-5-carboxyvaleramido)-7α-methoxy-3-cephem-4-carboxylic acid (purity 75%). The mixture was stirred on an oil bath at an internal temperature of 70°–90° C. for 5 minutes, after which it was quickly cooled and 20 ml of water and 30 ml of ethyl acetate were added. The pH of the aqueous phase was adjusted to a value of 2 by addition of dilute hydrochloric acid and then the ethyl acetate phase was separated off and the aqueous phase was extracted twice, each time with 30 ml of ethyl acetate. The extracts were combined and then the solvent was evaporated off under reduced pressure. 30 ml of diisopropyl ether were added to the oily residue and the mixture was stirred to give a powder. The powder was collected by filtration and dried to give 2.9 g (yield 80.7%) of 7β-(D-5-isobutoxycarbonylamino-5-carboxyvaleramido)-7α-methoxy-3-(1-methyl-1H-tetrazol-5-yl)thiomethyl-3-cephem-4-carboxylic acid (purity 69%).

Nuclear Magnetic Resonance Spectrum (CD$_3$COCD$_3$) δ ppm: 0.83, 0.93 (doublet, 6H); 1.52–2.77 (multiplet, 7H); 3.51 (singlet, 3H); 4.03 (singlet, 3H); 5.15 (singlet, 1H).

EXAMPLE 7

1.4 g of 1-methyl-5-mercaptotetrazole and 0.9 ml of water were added to 1.8 g of 3-carbamoyloxymethyl-7β-cyanomethylthioacetamido-7α-methoxy-3-cephem-4-carboxylic acid, and then the mixture was stirred on an oil bath at an internal temperature of 85°–90° C. for 5 minutes. The reagents melted to form an oil; after cooling this oil, 20 ml of water were added and the mixture was adjusted to a pH of 2.0 and extracted three times, each time with 30 ml of ethyl acetate. The extracts were combined and then the ethyl acetate was distilled off under reduced pressure. The residue was dissolved in 20 ml of acetone, and 4.5 ml of a 1 mmole/ml solution of sodium 2-ethylhexanoate in ethyl acetate were added to the resulting solution. The solvent was evaporated off and ethyl acetate was added to the residue. The mixture was stirred to give a powder, which was collected by filtration, washed with ethyl acetate and then dried to give 1.7 g (yield 79.7%) of sodium 7β-cyanomethylthioacetamido-7α-methoxy-3-(1-methyl-1H-tetrazol-5-yl)thiomethyl-3-cephem-4-carboxylate.

Nuclear Magnetic Resonance Spectrum (D$_2$O) δ ppm: 3.25–3.90 (quartet, 2H); 3.60 (singlet, 3H); 3.68 (singlet, 2H); 3.73 (singlet, 2H); 4.08 (singlet, 3H); 5.2 (singlet, 1H).

EXAMPLE 8

Following the procedure of Example 6, 2.0 g of 3-carbamoyloxymethyl-7α-methoxy-7β-(D-5-methoxycarbonylamino-5-carboxyvaleramido)-3-cephem-4-carboxylic acid (purity 81%) were reacted with 1.0 g of 1-methyl-5-mercaptotetrazole in the presence of 0.5 ml of water for 6 minutes at an internal temperature of 75°–90° C. to give 1.8 g (yield 79%) of 7α-methoxy-7β-

(D-5-methoxycarbonylamino-5-carboxyvaleramido)-3-(1-methyl-1H-tetrazol-5-yl)thiomethyl-3-cephem-4-carboxylic acid of purity 79%.

Nuclear Magnetic Resonance Spectrum (CD$_3$COCD$_3$) δ ppm: 1.35–2.68 (multiplet, 7H); 3.56 (singlet, 3H); 3.70 (singlet, 3H); 4.07 (singlet, 3H); 5.15 (singlet, 1H).

EXAMPLE 9

Following the procedure of Example 6, 2.5 g of 3-carbamoyloxymethyl-7β-(D-5-isopropoxycarbonylamino-5-carboxyvaleramido)-7α-methoxy-3-cephem-4-carboxylic acid (purity 78%) were reacted with 1.3 g of 1-methyl-5-mercaptotetrazole in the presence of 2.0 ml of water for 7 minutes at an internal temperature of 75°–90° C. to give 2.3 g (yield 80%) of 7β-(D-5-isopropoxycarbonylamino-5-carboxyvaleramido)-7α-methoxy-3-(1-methyl-1H-tetrazol-5-yl)thiomethyl-3-cephem-4-carboxylic acid of purity 74%.

Nuclear Magnetic Resonance Spectrum (CD$_3$COCD$_3$) δ ppm: 1.12–1.22 (doublet, 6H); 1.67–2.67 (multiplet, 7H); 3.37–3.98 (quartet, 2H); 3.50 (singlet, 3H); 4.0 (singlet, 3H); 4.2–4.65 (quartet, 2H); 5.07 (singlet, 1H).

EXAMPLE 10

Following the procedure described in Example 6, 2.5 g of 3-carbamoyloxymethyl-7β-(D-5-isobutoxycarbonylamino-5-carboxyvaleramido)-7α-methoxy-3-cephem-4-carboxylic acid were reacted with 2.0 g of 2-methyl-5-mercapto-1,3,4-thiadiazole in the presence of 1.2 ml of water for 6 minutes at an internal temperature of 75°–90° C. to give 2.4 g (yield 87.4%) of 7β-(D-5-isobutoxycarbonylamino-5-carboxyvaleramido)-7α-methoxy-3-(1-methyl-1,3,4-thiadiazol-5-yl)thiomethyl-3-cephem-4-carboxylic acid.

Nuclear Magnetic Resonance Spectrum (CD$_3$COCD$_3$) δ ppm: 1.08, 1.18 (doublet, 6H); 1.6–2.6 (multiplet, 7H); 2.76 (singlet, 3H); 3.57 (singlet, 3H); 5.11 (singlet, 1H).

EXAMPLE 11

Following the procedure described in Example 6, 3.0 g of 3-carbamoyloxymethyl-7α-methoxy-7β-thienylacetamido-3-cephem-4-carboxylic acid were reacted with 1.5 g of 1-methyl-5-mercaptotetrazole in the presence of 1.5 ml of water for 6 minutes at an internal temperature of 75°–90° C. to give 2.9 g (yield 85.6%) of 7α-methoxy-3-(1-methyl-1H-tetrazol-5-yl)thiomethyl-7β-thienylacetamido-3-cephem-4-carboxylic acid.

Nuclear Magnetic Resonance Spectrum (CD$_3$COCD$_3$) δ ppm: 3.48 (singlet, 3H); 3.98 (singlet, 2H); 4.0 (singlet, 3H); 4.22–4.73 (quartet, 2H); 5.11 (singlet, 1H); 6.91–7.50 (multiplet, 3H).

EXAMPLE 12

10 g of 3-carbamoyloxymethyl-7α-methoxy-7β-(D-5-p-nitrobenzoylamino-5-carboxyvaleramido)-3-cephem-4-carboxylic acid (purity 84.5%) were mixed with 30 g of 1-methyl-5-mercaptotetrazole and 1 ml of water and the mixture was reacted on an oil bath heated to 100° C. at an internal temperature of 75°–80° C. for 10 minutes, with vigorous stirring; during this time, the reaction mixture was subjected to reduced pressure and water continuously distilled off when the internal temperature exceeded 75° C. As the reaction came to an end, the reaction mixture began to solidify and substantially solidified in about 10 minutes. After completion of the reaction, 100 ml of water, 100 ml of ethyl acetate and 55 g of sodium chloride were added to the reaction mixture and then the aqueous phase was adjusted to a pH value of 1.8 by addition of 6N hydrochloric acid. The ethyl acetate phase was separated off and the aqueous phase was extracted three times, each time with 80 ml of ethyl acetate. The separated ethyl acetate phase and the extracts were combined and the mixture was concentrated by evaporation under reduced pressure. The residual oily substance was stirred with 500 ml of diisopropyl ether to solidify it and this solid was then recovered by filtration and washed with diisopropyl ether. The solid was then dissolved in 50 ml of acetone and insolubles were filtered off. The acetone was distilled off under reduced pressure and the resulting oil was then dried to afford 13.8 g (yield 93.1%) of 7α-methoxy-3-(1-methyl-1H-tetrazol-5-yl)thiomethyl-7β-(D-5-p-nitrobenzoylamino-5-carboxyvaleramido)-3-cephem-4-carboxylic acid (purity 62.3%) in the form of a powder.

2 g of the compound thus obtained were dissolved in 4 ml of acetone, and then 100 ml of ethyl acetate were added to the solution. The small quantity of insolubles was filtered off and then the filtrate was evaporated under reduced pressure until it started to become turbid. At this point, it was allowed to stand overnight at room temperature, whereupon white columnar crystals separated out. These crystals were recovered by filtration, washed with ethyl acetate and then dried to give a pure sample of the compound of the invention containing 1 mole of ethyl acetate of crystallization per mole of compound. Melting point 160° C. (with decomposition).

Elemental Analysis Calculated for C$_{24}$H$_{28}$N$_8$O$_{10}$S$_2$·C$_4$H$_8$O$_2$: C, 45.52%; H, 4.64%; N, 15.17%; S, 8.68%. Found: C, 45.65%; H, 4.76%; N, 15.03%; S, 8.46%.

Nuclear Magnetic Resonance Spectrum (CD$_3$COCD$_3$) δ ppm: 1.12–1.35 (triplet, 3H); 1.83–2.8 (multiplet, 7H); 2.0 (singlet, 3H); 3.57 (singlet, 3H); 4.06 (singlet, 3H); 3.42–4.06 (quartet, 2H, J=18 Hz); 4.23–4.77 (quartet, 2H, J=114 Hz); 5.18 (singlet, 1H); 8.2–8.63 (multiplet, 4H).

COMPARATIVE EXAMPLE

In this Comparative Example, the same compound was prepared as was prepared in Example 12 and the same starting materials were employed; however, the process used was a prior art process, in which the reaction takes place in the presence of a substantial quantity of water.

3.0 g of 3-carbamoyloxymethyl-7α-methoxy-7β-(D-5-p-nitrobenzoylamino-5-carboxyvaleramido)-3-cephem-4-carboxylic acid (purity 84.5%) were mixed with 3.0 g of 1-methyl-5-mercaptotetrazole and 90 ml of water and then the mixture was adjusted to a pH of 5.0 by the addition of 28% v/v aqueous ammonia. The mixture was stirred at an internal temperature of 65° C. for 3 hours. After ice-cooling the mixture, its pH value was adjusted to 2.0 by the addition of 6N hydrochloric acid and the mixture was extracted 5 times, each time with 50 ml of ethyl acetate. The combined extracts were concentrated by evaporation under reduced pressure and the residual oil was thoroughly stirred with 80 ml of diisopropyl ether to form a solid. This solid was recovered by filtration and dried to give 2.4 g (yield 24.7%) of 7α-methoxy-3-(1-methyl-1H-tetrazol-5-yl)thiomethyl-7β-(D-5-p-nitrobenzoylamino-5-carboxyvaleramido)-3-cephem-4-carboxylic acid having a purity of 28.5%.

When the same procedure as described above was repeated, but effecting the reaction at an internal temperature of 75°-80° C. and for a period of 20 minutes, the same product was obtained in a yield of 18%.

We claim:

1. A non-catalytic process for the preparation of a cephalosporin derivative of formula (I):

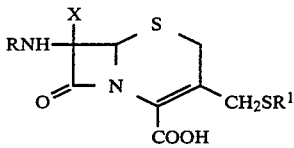

wherein:

R is a hydrogen atom; a substituted acetyl group in which the substituent is amino group, substituted amino group, carboxyl group, halogen atom, sulfonyl group, hydroxy group, heterocyclic group, heterocyclic-thio group, heterocyclic-oxy group, substituted or unsubstituted alkylthio group or alkynylthio group; a substituted valeryl group in which the substituent is nitro group, amino group or carboxyl group; or a substituted benzoyl group in which the substituent is amino group, hydroxyl group or sulfo group;

$R^1$ is a substituted or unsubstituted tetrazole, thiadiazole or triazole group; or the group

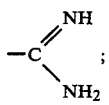

and

X is a hydrogen atom or an alkoxy group;

said process consisting essentially of heating a cephalosporin compound of formula II:

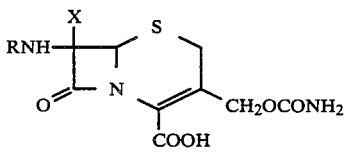

with a thiol of formula III

 III under (i) (a) anhydrous conditions or (i) (b) in the presence of water in an amount that does not exceed 2 times the weight of said compound of formula II and (ii) in the absence of an organic solvent.

2. The process of claim 1, wherein the reaction is carried out at a temperature of from 50° to 150° C.

3. The process of claim 1, wherein the reaction is carried out in the presence of water in an amount less than 5 times the weight of said compound of formula III.

4. The process of claim 1 wherein the reaction is carried out under anhydrous conditions.

5. The process of claim 3, wherein the reaction is carried out at a temperature of from 65° to 90° C.

6. The process of claim 1, wherein said cephalosporin derivative of the formula I is 7α-methoxy-3-(1-methyl-1H-tetrazol-5-yl)thiomethyl-7β-(1,3,4-thiadiazol-2-yl)thioacetamido-3-cephem-4-carboxylic acid.

7. The process of claim 1, wherein said cephalosporin derivative of the formula I is 7β-(isoxazol-5-yloxy)acetamido-7α-methoxy-3-(1-methyl-1H-tetrazol-5-yl)thiomethyl-3-cephem-4-carboxylic acid.

8. The process of claim 1, wherein said cephalosporin derivative of the formula I is 7α-methoxy-3-(1-methyl-1H-tetrazol-5-yl)thiomethyl-7β-propargylthioacetamido-3-cephem-4-carboxylic acid.

9. The process of claim 1, wherein said cephalosporin derivative of the formula I is 7β-cyanomethylthioacetamido-7α-methoxy-3-(1-methyl-1H-tetrazol-5-yl)thiomethyl-3-cephem-4-carboxylic acid.

10. The process of claim 1, wherein said cephalosporin derivative of the formula I is 7α-methoxy-3-(1-methyl-1H-tetrazol-5-yl)thiomethyl-7β-(5-methyl-1,3,4-thiadiazol-2-yl)thioacetamido-3-cephem-4-carboxylic acid.

11. The process of claim 1, wherein said cephalosporin derivative of the formula I is 7β-(D-5-amino-5-carboxyvaleramido)-7α-methoxy-3-(1-methyl-1H-tetrazol-5-yl)thiomethyl-3-cephem-4-carboxylic acid.

12. The process of claim 1, wherein said cephalosporin derivative of the formula I is 7β-(D-5-isobutoxycarbonylamino-5-carboxyvaleramindo)-7α-methoxy-3-(1-methyl-1H-tetrazol-5-yl)thiomethyl-3-cephem-4-carboxylic acid.

13. The process of claim 1, wherein said cephalosporin derivative of the formula I is 7α-methoxyl-3-(1-methyl-1H-tetrazol-5-yl)thiomethyl-7β-(D-5-p-nitrobenzoylamino-5-carboxylvaleramido)-3-cephem-4-carboxylic acid.

* * * * *